US011212955B2

(12) United States Patent
Schoeny et al.

(10) Patent No.: US 11,212,955 B2
(45) Date of Patent: Jan. 4, 2022

(54) SYSTEM AND METHOD FOR MONITORING SOIL CONDITIONS BASED ON DATA RECEIVED FROM A SENSOR MOUNTED WITHIN A GROUND-ENGAGING TOOL TOOTH

(71) Applicant: CNH Industrial America LLC, New Holland, PA (US)

(72) Inventors: Christopher Schoeny, Minooka, IL (US); Trevor Stanhope, Palos Hills, IL (US)

(73) Assignee: CNH Industrial America LLC, New Holland, PA (US)

( * ) Notice: Subject to any disclaimer, the term of this patent is extended or adjusted under 35 U.S.C. 154(b) by 277 days.

(21) Appl. No.: 16/442,160

(22) Filed: Jun. 14, 2019

(65) Prior Publication Data

US 2020/0390025 A1 Dec. 17, 2020

(51) Int. Cl.
*A01B 79/00* (2006.01)
*A01B 47/00* (2006.01)
(Continued)

(52) U.S. Cl.
CPC ............ *A01B 79/005* (2013.01); *A01B 47/00* (2013.01); *A01C 5/066* (2013.01); *A01C 7/08* (2013.01);
(Continued)

(58) Field of Classification Search
CPC ....... A01B 47/00; A01B 79/005; A01C 5/066; A01C 7/08; A01C 7/203
See application file for complete search history.

(56) References Cited

U.S. PATENT DOCUMENTS 5,044,756 A * 9/1991 Gaultney ........... G01N 21/8507
356/446
5,355,815 A 10/1994 Monson
(Continued)

FOREIGN PATENT DOCUMENTS

CN 202421071 9/2012
CN 108362677 8/2018
(Continued)

OTHER PUBLICATIONS

Chang, C.W. et al., "Near-Infrared Reflectance Spectroscopy-Principal Components Regression Analyses of Soil Properties," Soil Science Society of America, vol. 65, No. 2, pp. 480.
(Continued)

*Primary Examiner* — Thomas B Will
*Assistant Examiner* — Ian A Normile
(74) *Attorney, Agent, or Firm* — Rebecca L. Henkel; Rickard K. DeMille (57) ABSTRACT

In one aspect, a system for monitoring soil composition within a field using an agricultural machine may include a ground-engaging tool configured to rotate relative to soil within a field as the agricultural machine is moved across the field. The ground-engaging tool may, in turn, include a tooth defining a cavity therein, with the cavity including an opening. Furthermore, the system may include a sensor positioned within the cavity, with the sensor configured emit an output signal through the opening for reflection off of the soil within the field. The sensor may also be configured to detect the reflected output signal as a return signal, with a parameter of the return signal being indicative of a soil composition of the soil within the field.

14 Claims, 6 Drawing Sheets

(51) Int. Cl.
  *A01C 5/06* (2006.01)
  *A01C 7/20* (2006.01)
  *G01N 33/24* (2006.01)
  *A01C 7/08* (2006.01)

(52) U.S. Cl.
  CPC ............. *A01C 7/203* (2013.01); *G01N 33/24* (2013.01); *G01N 2033/245* (2013.01)

(56) References Cited

U.S. PATENT DOCUMENTS

| | | | |
|---|---|---|---|
| 5,837,997 | A | 11/1998 | Beck et al. |
| 7,336,351 | B1 | 2/2008 | Sweatt et al. |
| 8,451,449 | B2 | 5/2013 | Holland |
| 9,255,878 | B2 | 2/2016 | Preiner et al. |
| 9,743,574 | B1 | 8/2017 | Maxton et al. |
| 9,743,578 | B2 | 8/2017 | Blomme et al. |
| 9,891,155 | B2 | 2/2018 | Eising |
| 9,924,629 | B2 | 3/2018 | Batcheller et al. |
| 9,964,396 | B1 | 5/2018 | Scott et al. |
| 9,964,532 | B2 | 5/2018 | Bauer-Reich et al. |
| 2007/0013908 | A1 | 1/2007 | Lee et al. |
| 2011/0155031 | A1* | 6/2011 | Arnett .................. A01C 5/066 111/193 |
| 2012/0092663 | A1 | 4/2012 | Kull et al. |
| 2016/0223511 | A1 | 8/2016 | Koshnick et al. |
| 2017/0086359 | A1* | 3/2017 | Landphair ............. A01C 7/203 |
| 2017/0086361 | A1* | 3/2017 | Landphair ............. A01C 7/205 |
| 2017/0090068 | A1 | 3/2017 | Xiang et al. |
| 2018/0168094 | A1 | 6/2018 | Koch et al. |
| 2018/0206393 | A1 | 7/2018 | Stoller et al. |
| 2018/0292339 | A1 | 10/2018 | Gunzenhauser |
| 2020/0225206 | A1* | 7/2020 | Strnad ................... A01C 21/00 |

FOREIGN PATENT DOCUMENTS

| | | | |
|---|---|---|---|
| DE | 19507119 | | 9/1995 |
| GB | 190926583 | * | 10/1910 ............. A01B 21/04 |
| WO | WO1995015487 | | 6/1995 |

OTHER PUBLICATIONS

Martin, Madhavi Z. et al., "Laser-Induced Breakdown Spectroscopy for the Environmental Determination of Total Carbon and Nitrogen in Soils," Applied Optics, vol. 42, Issue 12, 2003, pp. 2072-2077.

Mouazen, A.M. et al., "Comparison Among Principal Component, Partial Least Squares and Back Propagation Neural Network Analyses for Accuracy of Measurement of Selected Soil Properties with Visible and Near Infrared Spectroscopy," Geoderma, vol. 158, Issues 1-2, Aug. 15, 2010, pp. 23-31.

* cited by examiner

SYSTEM AND METHOD FOR MONITORING SOIL CONDITIONS BASED ON DATA RECEIVED FROM A SENSOR MOUNTED WITHIN A GROUND-ENGAGING TOOL TOOTH

FIELD OF THE INVENTION

The present disclosure generally relates to agricultural machines and, more particularly, to systems and methods for monitoring soil conditions within a field using an agricultural machine based on data received from a sensor installed or otherwise mounted within a tooth of a rotating ground-engaging tool of the machine.

BACKGROUND OF THE INVENTION

Modern farming practices strive to increase yields of agricultural fields. In this respect, seed-planting implements are towed behind a tractor or other work vehicle to disperse seed throughout a field. For example, seed-planting implements typically include one or more furrow-opening tools (e.g., a disc opener(s) or a hoe(s)) that excavate a furrow or trench in the soil. One or more dispensing devices of the seed-planting implements may, in turn, deposit the seeds into the furrow(s). After deposition of the seeds, a one or more furrow-closing tools (e.g., a closing disc(s) or a closing wheel(s)) may close the furrow in the soil, such as by pushing the excavated soil into the furrow.

The soil composition of the field, such as the organic matter, residue, and/or moisture content, may affect the operation of the seed-planting implement. For example, the desired penetration depth of and/or the force applied to the furrow-closing tool(s) may be based on the soil composition of the field. However, due to varying conditions across the field and/or other factors, it may be necessary to adjust one or more operating parameters of the seed-planting implement during a seed-planting operation to ensure proper operation of the implement. In this regard, systems and methods for monitoring the soil composition within a field have been developed. However, further improvements to such systems and methods are needed.

Accordingly, an improved system and method for monitoring soil conditions within a field would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for monitoring soil composition within a field using an agricultural machine. The system may include a ground-engaging tool configured to rotate relative to soil within a field as the agricultural machine is moved across the field. The ground-engaging tool may, in turn, including a tooth defining a cavity therein, with the cavity including an opening. Furthermore, the system may include a sensor positioned within the cavity, with the sensor configured emit an output signal through the opening for reflection off of the soil within the field. The sensor may also be configured to detect the reflected output signal as a return signal, with a parameter of the return signal being indicative of a soil composition of the soil within the field.

In another aspect, the present subject matter is directed to a method for monitoring soil composition within a field using an agricultural machine. The agricultural machine may include a ground-engaging tool configured to rotate relative to soil within a field as the agricultural machine is moved across the field. The ground-engaging tool may, in turn, include a tooth defining a cavity therein, with the cavity including an opening. The method may include receiving, with one or more computing devices, data from a sensor positioned within the cavity. The sensor may be configured to emit an output signal through the opening for reflection off of the soil within the field and detect the reflected output signal as a return signal. The method may also include determining, with the one or more computing devices, a soil composition of the soil based on the received data. Furthermore, when the determined soil composition of the soil differs from a predetermined range of soil compositions, the method may include initiating, with the one or more computing devices, a control action associated with adjusting an operating parameter of the agricultural machine.

In a further aspect, the present subject matter is directed to a seed-planting implement. The seed-planting implement may include a frame and a furrow-opening tool coupled to the frame, with the furrow-opening tool configured to form a furrow in the soil as the seed-planting implement is moved across the field. The seed-planting implement may also include a closing disc coupled to the frame, with the closing disc configured to rotate relative to soil within a field as the seed-planting implement is moved across the field in a manner that closes the furrow. The closing disc may, in turn, define a cavity therein, with the cavity including an opening. Additionally, the seed-planting implement may include a sensor positioned within the cavity. The sensor may be configured emit an output signal through the opening for reflection off of the soil within the field. Moreover, the sensor may be further configured to detect the reflected output signal as a return signal, with a parameter of the return signal being indicative of a soil composition of the soil within the field.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for monitoring soil composition within a field using an agricultural machine. Specifically, in several embodiments, as the agricultural machine is moved across a field, a controller of the disclosed system may be configured to receive data from a soil sensor installed or otherwise positioned within a cavity defined by a tooth of a rotating ground-engaging tool (e.g., a closing disc) of the machine. For example, in one embodiment, the cavity may include an opening defined by a surface of tooth. The soil sensor may, in turn, be configured to emit an output signal(s) (e.g., an electromagnetic radiation signal(s)) through the opening for reflection off of the soil within the field. Moreover, the soil sensor may be configured to detect the reflected output signal(s) as a return signal(s), with one or more parameters (e.g., spectral parameter(s)) of the return signal(s) being indicative of the composition of the soil (e.g., the amount of organic matter, residue, and/or moisture within the soil). In this regard, the controller may be configured to determine the composition of the soil within the field across which the machine is being moved based on the received data. Thereafter, when the determined soil composition differs from a predetermined range of soil compositions, the controller may be configured to initiate one or more control actions associated with adjusting an operating parameter of the agricultural machine (e.g., the penetration depth(s) of and/or the force being applied to the ground-engaging tool(s) of the machine).

The present subject matter will generally be described herein in the context of monitoring soil composition using a soil sensor positioned within a cavity defined by a tooth of closing disc mounted on a seed-planting implement, such as a seeder. However, it should be appreciated that the disclosed system and method may also be used to monitor soil composition using a soil sensor positioned within a cavity defined by any other suitable ground-engaging disc (e.g., a disc opener, a harrow disc, and/or the like) mounted on any other type of agricultural machine, such as another suitable type of implement (e.g., a tillage implement, a planter, a fertilizer, and/or the like) and/or a suitable agricultural vehicle (e.g., tractor, a harvester, a self-propelled sprayer, and/or the like).

Figure 1:
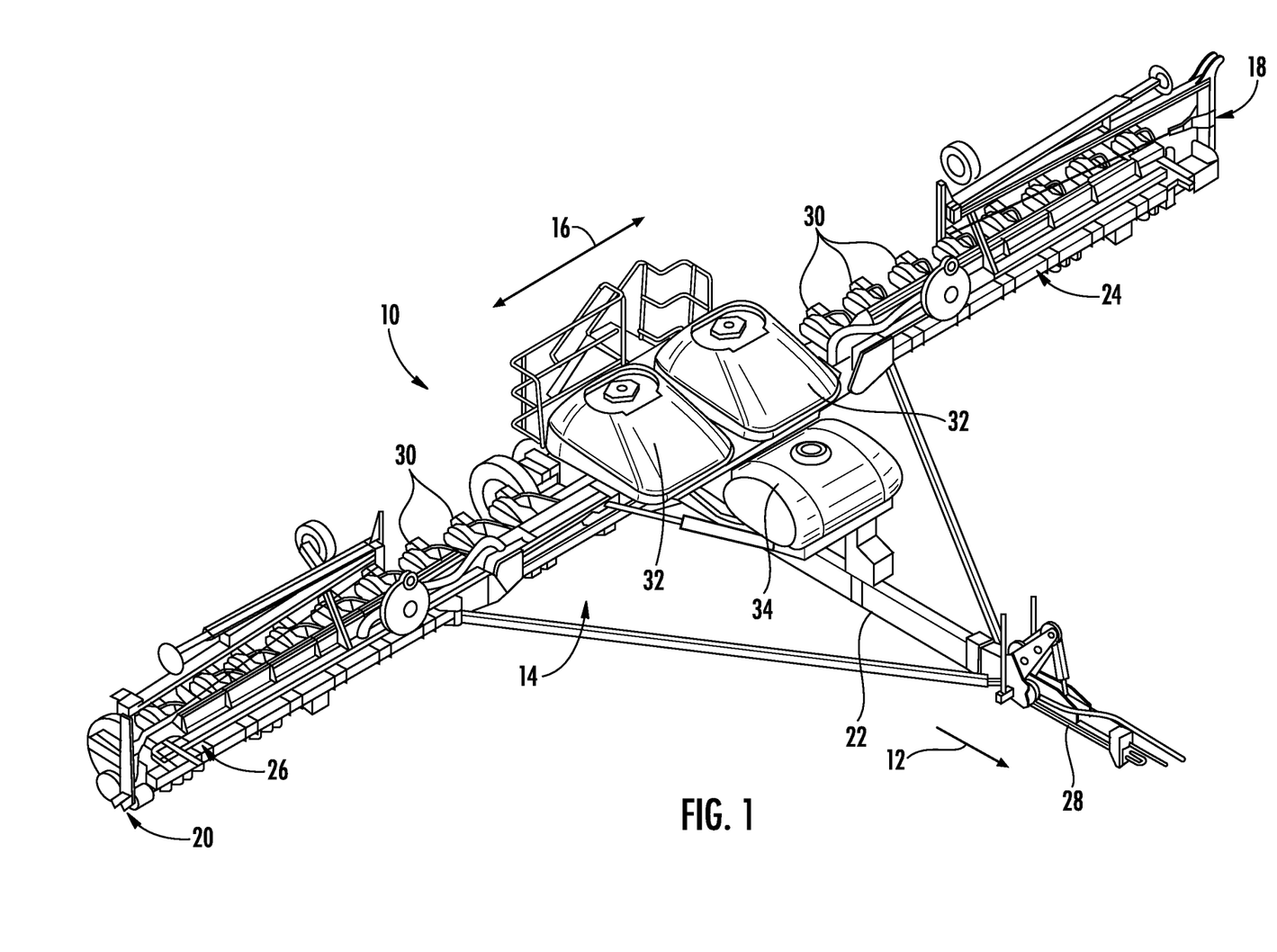
FIG. 1 illustrates a perspective view of one embodiment of an agricultural machine in accordance with aspects of the present subject matter.

Referring now to the drawings, FIG. 1 illustrates a top view of one embodiment of a seed-planting implement in accordance with aspects of the present subject matter. As shown in the illustrated embodiment, the implement 10 may be configured to be towed across a field in a direction of travel (e.g., as indicated by arrow 12) by a work vehicle (not shown), such as a tractor or other agricultural work vehicle.

As shown in FIG. 1, the implement 10 may include a toolbar 14 configured to support and/or couple to one or more components of the implement 10. Specifically, in several embodiments, the toolbar 14 may extend along a lateral direction 16 between a first side 18 of the implement 10 and a second side 20 of the implement 10. As shown, the toolbar 16 may include a center section 22, a first wing section 24, and a second wing section 26. In one embodiment, the wing sections 24, 26 may be pivotably coupled to the center section 22 in a manner that permits the wing sections 24, 26 to fold forward to reduce the lateral width of the implement 10, such as during storage or transportation of the implement 10 on a road. Furthermore, a tow bar 28 may be coupled to the center section 22 to allow the implement 10 to be towed by the work vehicle in the direction of travel 12.

Additionally, as shown in FIG. 1, the wing sections 24, 26 and the center section 22 may generally be configured to support a plurality of seed-planting units or row units 30. As will be described below, each row unit 30 may be configured to deposit seeds at a desired depth beneath the soil surface and at a desired seed spacing as the implement 10 is moved across the field, thereby establishing rows of planted seeds. In some embodiments, the bulk of the seeds to be planted may be stored in one or more hoppers or seed tanks 32 mounted on or otherwise supported by the toolbar 14. Thus, as seeds are planted by the row units 30, a pneumatic distribution system (not shown) may distribute additional seeds from the seed tanks 32 to the individual row units 30. Additionally, one or more fluid tanks 34 mounted on or otherwise supported by the toolbar 14 may store agricultural fluids, such as insecticides, herbicides, fungicides, fertilizers, and/or the like, which may be sprayed onto the seeds during planting.

It should be appreciated that, for purposes of illustration, only a portion of the row units 30 of the implement 10 have been shown in FIG. 1. In general, the implement 10 may include any number of row units 30, such as six, eight, twelve, sixteen, twenty-four, thirty-two, or thirty-six row units. In addition, it should be appreciated that the lateral spacing between row units 30 may be selected based on the type of crop being planted. For example, the row units 30 may be spaced approximately thirty inches from one another for planting corn, and approximately fifteen inches from one another for planting soybeans.

Figure 2:
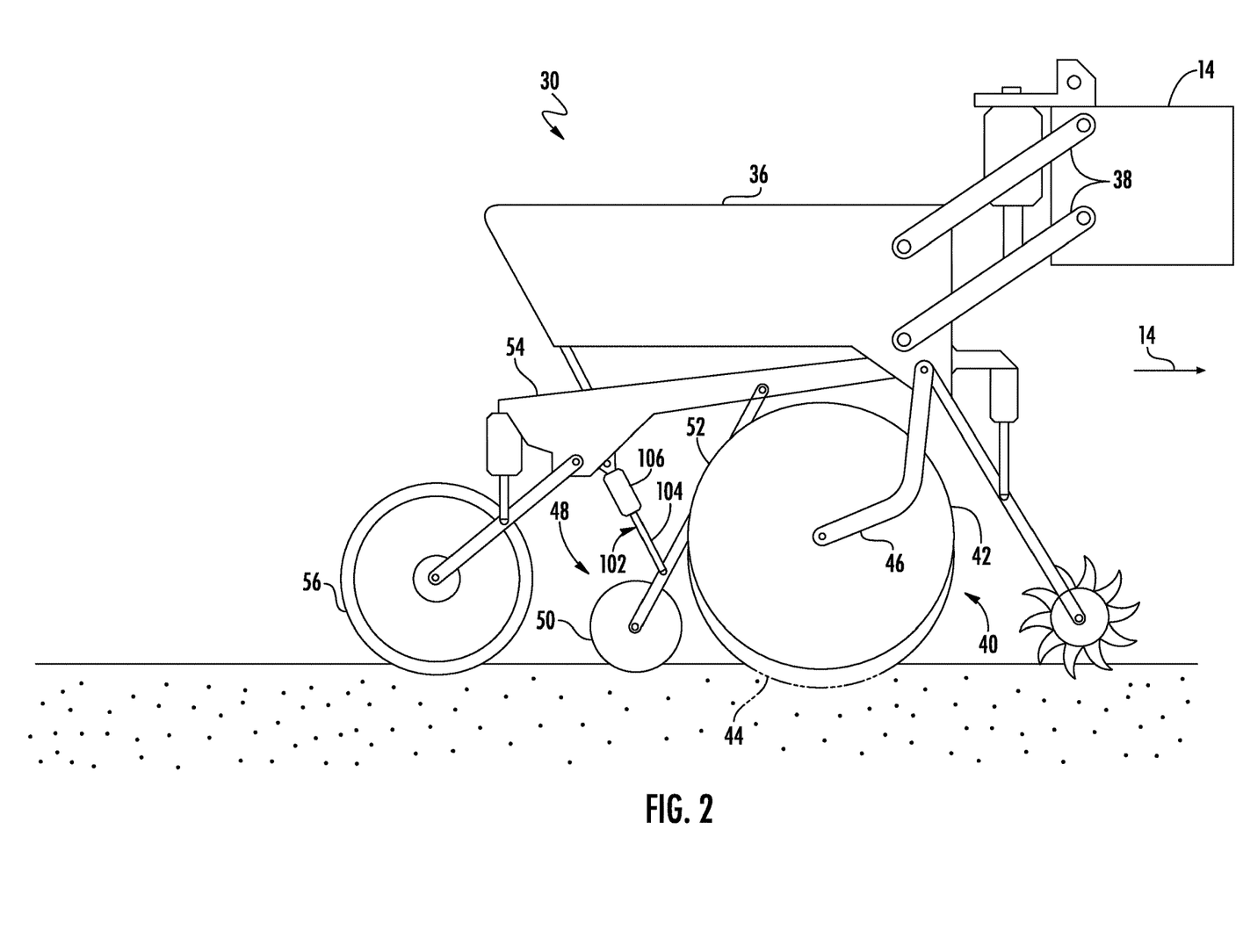
FIG. 2 illustrates a side view of one embodiment of a row unit of an agricultural machine in accordance with aspects of the present subject matter.

Referring now to FIG. 2, a side view of one embodiment of a row unit 30 is illustrated in accordance with aspects of the present subject matter. As shown, the row unit 30 may include a frame 36 adjustably coupled to the toolbar 14 by links 38. For example, one end of each link 38 may be pivotably coupled to the frame 36, while an opposed end of each link 38 may be pivotably coupled to the toolbar 14. In one embodiment, the links 38 may be parallel. However, in alternative embodiments, the row unit 30 may be coupled to the toolbar 14 in any other suitable manner.

As shown, the row unit 30 may include a furrow-opening assembly 40. For example, in one embodiment, the furrow-opening assembly 40 may include a gauge wheel 42 and one or more disc openers 44 configured to excavate a furrow or trench in the soil. In general, the gauge wheel 42 may be configured to engage the top surface of the soil as the implement 10 is moved across the field. As such, the height of the disc opener(s) 44 may be adjusted with respect to the position of the gauge wheel 42 to set the desired depth of the furrow being excavated. Furthermore, the furrow-opening assembly 40 may include a support arm 46 configured to adjustably couple the gauge wheel 42 to the frame 36. For example, one end of the support arm 46 may be pivotably coupled to the gauge wheel 42, while an opposed end of the support arm 46 may be pivotably coupled to the frame 36. Additionally, the disc opener(s) 44 may be coupled (e.g., bolted) to the frame 36. However, in alternative embodiments, the gauge wheel 42 and the disc opener(s) 44 may be coupled to the frame 36 in any other suitable manner. Furthermore, the furrow-opening assembly 40 may include any other suitable type of furrow-opening tool(s), such as a hoe(s).

Moreover, as shown, the row unit 30 may include a furrow-closing assembly 48. Specifically, in several embodiments, the furrow-closing assembly 48 may include a pair of closing discs 50 (only one is shown in FIG. 2) positioned relative to each other in a manner that permits soil to flow between the discs 50 as the implement 10 is moved across the field. As such, the closing discs 50 may be configured to penetrate the soil in a manner that collapses the furrow, thereby closing the furrow after seeds have been deposited therein. Furthermore, the furrow-closing assembly 48 may include a support arm 52 configured to adjustably couple the closing discs 50 to the frame 36. For example, one end of the support arm 52 may be pivotably coupled to the closing discs 50, while an opposed end of the support arm 52 may be pivotably coupled to a chassis arm 54, which is, in turn, coupled to the frame 36. However, in alternative embodiments, the closing discs 50 may be coupled to the frame 36 in any other suitable manner. Furthermore, in alternative embodiments, the furrow-closing assembly 48 may include any other suitable number of closing discs 50, such as one closing disc 50 or three or more closing discs 50. Additionally, the row unit 30 may include a press wheel 56 configured to roll over the closed furrow to firm the soil over the seed and promote favorable seed-to-soil contact.

Additionally, in several embodiments, a furrow-closing assembly actuator 102 may be configured to move or otherwise adjust the position of the closing discs 50 relative to the frame 36. For example, as shown in the illustrated embodiment, a first end of the actuator 102 (e.g., a rod 104 of the actuator 102) may be coupled to the support arm 52 of the furrow-closing assembly 48, while a second end of the actuator 102 (e.g., the cylinder 106 of the actuator 102) may be coupled to the chassis arm 54, which is, in turn, coupled to the frame 36. The rod 104 of the actuator 102 may be configured to extend and/or retract relative to the cylinder 106 to adjust the position of the closing discs 50 relative to the frame 36. Furthermore, the actuator 102 may be configured to apply a force to the closing discs 50, which may, in turn, cause the closing discs 50 to penetrate the soil. For example, the actuator 102 may increase the penetration depth of the closing discs 50 by increasing the force applied thereto. Conversely, the actuator 102 may reduce the penetration depth of the closing discs 50 by decreasing the force applied thereto. In the illustrated embodiment, the actuator 102 corresponds to a fluid-driven actuator, such as hydraulic or pneumatic cylinder. However, it should be appreciated that the actuator 102 may correspond to any other suitable type of actuator, such as an electric linear actuator.

Figure 3:
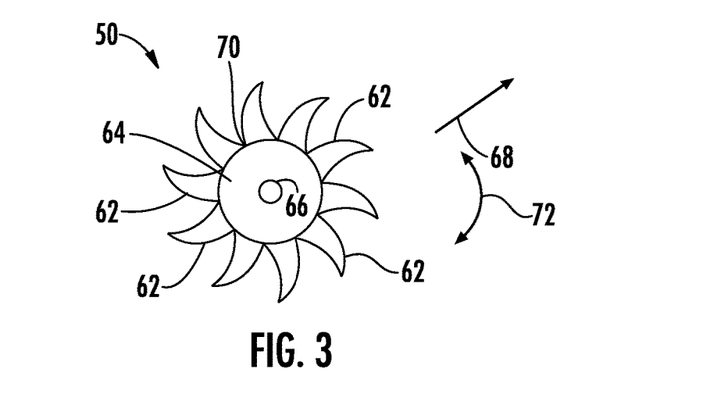
FIG. 3 illustrates a side view of one embodiment of a ground-engaging tool of an agricultural machine in accordance with aspects of the present subject matter, particularly illustrating the tool including a plurality of teeth.
Figure 4:
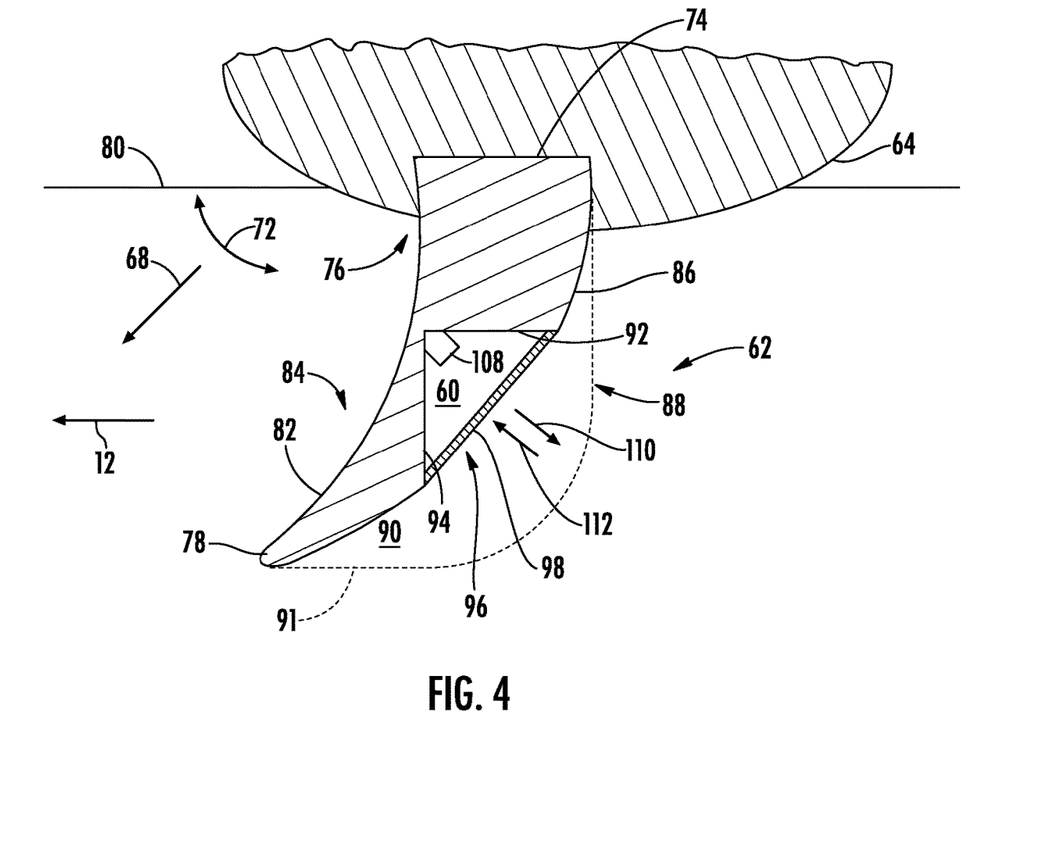
FIG. 4 illustrates a partial, cross-sectional view of the ground-engaging tool shown in FIG. 3, particularly illustrating a soil sensor positioned within a cavity defined by a tooth of the tool.

Referring now to FIGS. 3 and 4, differing views of one embodiment of a closing disc 50 are illustrated in accordance with aspects of the present subject matter. Specifically, FIG. 3 illustrates a side view of the closing disc 50. Additionally, FIG. 4 illustrates a partial, cross-sectional view of the closing disc 50, particularly illustrating a soil sensor 108 installed within a cavity 60 defined by a tooth 62 of the disc 50.

As shown in FIG. 3, the closing disc 50 may include a hub 64 and a plurality of teeth 62. Specifically, in several embodiments, the hub 64 may be rotatably coupled to an axle 66, which may, in turn, be coupled to the support arm 52. As such, the hub 64 may generally extend outward from the axle 66 in a radial direction (e.g., as indicated by arrow 68 in FIG. 3). In this regard, the closing disc 50 may be configured to rotate relative to the axle 66 and the support arm 52 as the implement 10 is moved across the field. Furthermore, the plurality of teeth 62 may extend outward from a radially outer edge 70 of the hub 64 at least partially in the radial direction 68. For example, in one embodiment, the teeth 62 may extend outward from the hub 64 in both the radial direction 68 and a circumferential direction (e.g., as indicated by arrow 72 in FIG. 3). In such an embodiment, the teeth 62 may be curved. However, in alternative embodiments, the teeth 60 may have any other suitable configuration such that the teeth 60 extend at least partially outward from the hub 64 in the radial direction 68 (e.g., a sawtooth configuration). Moreover, as shown, the teeth 62 may be spaced apart from each other along the radially outer edge 70 in the circumferential direction 72. Additionally, although the embodiment of the closing disc 50 shown in FIG. 3 includes eight teeth 62, it should be appreciated that the disc 50 may include any other suitable number of teeth 62.

Referring now to FIG. 4, one or more of the teeth 62 may be removably coupled to the hub 64. For example, in one embodiment, the hub 64 may define one or more slots or cavities 74 extending radially inward from the radially outer edge 70 of the hub 64. Each slot 74 may, in turn, receive a mounting end 76 of one of the teeth 62. Suitable fasteners (e.g., bolts, pins, and/or the like) may couple the tooth/teeth 62 to the hub 64 such that the mounting end(s) 76 of the tooth/teeth 62 is retained within the slot(s) 74. As will be described below, in several embodiments, the soil sensor 108 may be installed or otherwise positioned within a cavity 60 defined by a tooth 62 that is removably coupled to the hub 64. In this regard, the tooth 62 in which the soil sensor 108 is installed may be removed from the hub 64 when replacing the sensor 108 instead of removing the entire closing disc 50. However, in alternative embodiments, the teeth 62 may be integrally formed with the hub 64.

As shown in FIG. 4, the teeth 62 of the closing disc 50 may generally be configured to penetrate the ground as the implement 10 is moved across the field. Specifically, in several embodiments, each tooth 62 may include a tip 78 positioned at its radially outer end (i.e., the end of the tooth 62 that is opposite of the mounting end 76) and configured to pierce or otherwise penetrate a soil surface 80 of the field. Furthermore, as shown, each tooth 62 may include a leading surface 82 positioned on a forward side 84 of the tooth 62 relative to the direction of travel 12. Similarly, each tooth 62 may also include a trailing surface 86 positioned on an aft side 88 of the tooth 62 relative to the direction of travel 12.

As such, when a force is applied to the closing disc 50 (e.g., via the actuator 102) and the implement 10 is moved across the field, the disc 50 may rotate relative to the soil within the field such that the teeth 62 penetrate the soil surface 80 of the field.

Moreover, as the closing disc 50 rotates relative to the soil within the field, soil may flow around the teeth 62 in a manner that collapses or otherwise closes the furrow formed by the implement 10. For example, when the closing disc 50 rotates, the soil may initially contact the leading surfaces 82 of each tooth 62. A first portion of the soil may flow around one side of each tooth 62, while another portion of the soil may flow around the opposed side of each tooth 62. The portions of the soil around each side of each tooth 62 may converge aft of the trailing surface 86 of each tooth 62. In this regard, a void 90 in the soil may be formed underneath and/or behind each tooth 62 as the closing disc 50 rotates relative to the soil. For instance, as shown in FIG. 4, the void 90 may be defined between the trailing surface 86 of each tooth 62 and a location at which the portions of soil flowing around each tooth 62 converge (e.g., as indicated by dashed line 91 in FIG. 4).

Furthermore, one of the teeth 62 of the closing disc 50 may define a cavity 60 therein. As will be described below, a soil sensor 108 may be installed or otherwise positioned within the cavity 60. The soil sensor 108 may, in turn, be configured to emit an output signal(s) for reflection off of the soil and receive the reflected output signals as a return signal(s), with such return signals being indicative of the composition of the soil. Specifically, in several embodiments, the cavity 60 may be defined by a portion of the corresponding tooth 62 such that, when the closing disc 50 rotates relative to the soil, the cavity 60 is positioned beneath the soil surface 80. Furthermore, the cavity 60 may be positioned adjacent to the aft side 86 of the corresponding tooth 62. For example, as shown in FIG. 4, the cavity 60 may be at least partially defined by a top surface 92 that extends forward in the direction of travel 12 from the trailing surface 86 toward the leading surface 82. In one embodiment, the top surface 92 may generally be parallel to the soil surface. Moreover, the cavity 60 may be at least partially defined by a forward surface 94 that extends upward from the trailing surface 86 toward the hub 64. As such, the top and forward surfaces 92, 94 may be oriented perpendicularly relative to each other such that the surfaces 92, 94 intersect at a generally right angle. In this regard, the cavity 60 may define a generally triangular cross-sectional shape. However, in alternative embodiments, the cavity 60 may have any other suitable configuration.

Additionally, the trailing surface 62 of the corresponding tooth 62 may define an opening 96 of the cavity 60. In general, the opening 96 permits access to the cavity 60 such that the soil sensor 108 may be installed therein. Furthermore, as will be described below, the opening 96 may permit the output signal(s) emitted by the sensor 108 to exit the cavity 60 and the reflected return signal(s) to enter the cavity 96. As shown in FIG. 4, the opening 96 may be positioned between the cavity 60 and the void 90 such that the output signal(s) are directed into the void 90.

In one embodiment, a covering or window 98 may be positioned within the opening 96 to prevent soil and/or moisture from entering the cavity 96 and potentially impacting the operation of the soil sensor 108. In this regard, the window 98 may correspond to any suitable device that may prevent soil/moisture from entering the cavity 96, while still allowing emitted output signal(s) to exit and reflected return signal(s) to enter the cavity 60. For example, in one embodiment, the window 98 may be a transparent or translucent component (e.g., a sheet/plate of polymeric material) that separates the cavity 60 from the void 90. Moreover, in the illustrated embodiment, the window 98 generally has a planar cross-section such that the output and/or return signals are not distorted thereby. However, in alternative embodiments, the cross-section of the window 98 may be curved (e.g., either in a concave or convex nature) such that the output and/or return signals are focused or dispersed. Furthermore, the window 98 may be any other suitable component that operates in a manner described above. In some embodiments, no window 98 may be positioned within the opening 96.

In accordance with aspects of the present subject matter, a soil sensor 108 may be installed or otherwise positioned within the cavity 60. In general, the soil sensor 108 may be configured to emit one or more output signals (e.g., as indicated by arrow 110 in FIG. 4) for reflection off of the soil. Specifically, as shown, the output signal(s) 110 emitted by the soil sensor 108 may travel through the cavity 60 and the opening/window 96/98 and into the void 90. Thereafter, the output signal(s) 110 may be reflected by the soil surface 91 defining the void 90 as a return signal(s) (e.g., as indicated by arrow 112 in FIG. 4) such that the return signal(s) 112 travel through the void 90 and the opening/window 96/98 and into cavity 60. As such, the soil sensor 108 may be configured to receive the reflected return signal(s) 112. Furthermore, the soil sensor 108 may be mounted or positioned within the cavity 60 in any suitable manner that permits the sensor 108 to emit the output signal(s) 110 into the void 90 and receive the reflected return signal(s) 112. For example, in the illustrated embodiment, the soil sensor 108 may be positioned within the cavity 60 at the intersection of the top and forward surfaces 92, 94 such that the output signal(s) 110 emitted by the sensor 108 are perpendicular to the opening/window 96/98. However, in alternative embodiments, the soil sensor 108 may be mounted on the top surface 92, the bottom surface 94, or at any other suitable surface or feature defining or within the cavity 60.

It should be appreciated that the soil sensor 108 may generally correspond to any suitable sensing device configured to function as described herein, such as by emitting one or more output signals for reflection off of the soil and by receiving or sensing the return signal(s). For example, in one embodiment, the soil sensor 108 may include an emitter(s) configured to emit an electromagnetic radiation signal(s), such as an ultraviolet radiation signal(s), a near-infrared radiation signal(s), a mid-infrared radiation signal(s), or a visible light signal(s) for reflection off of the soil. The soil sensor 108 may also include a receiver(s) configured to receive the reflected electromagnetic radiation signal(s). One or more spectral parameter(s) (e.g., the amplitude, frequency, and/or the like) of the reflected electromagnetic radiation signal(s) may, in turn, be indicative of the composition of the soil. In this regard, the emitter(s) may be configured as a light-emitting diode (LED(s)) or other electromagnetic radiation-emitting device(s) and the receiver(s) may be configured as a photo resistor(s) or other electromagnetic radiation-receiving device(s). However, in alternative embodiments, the soil sensor 108 may have any other suitable configuration and/or components.

Moreover, it should be appreciated that installation of the soil sensor 108 within the cavity 60 defined by the tooth 62 of the closing disc 50 may provide one or more technical advantages. For instance, by positioning the soil sensor 108 within the tooth 62, the soil sensor 108 may be replaced by removing the tooth 62 from the hub 64 of the closing disc 50 instead of removing the entire closing disc 50 from the implement 10, thereby reducing machine downtime. Furthermore, by positioning the cavity 60 within the tooth 62 such that it is located underneath the soil surface, ambient light (e.g., sunlight) may not interfere with the output and/or return signals 110, 112.

Additionally, it should be appreciated that the implement 10 may include one or more soil sensors 108. For example, in one embodiment, the implement 10 may only include one soil sensor 108. In such an embodiment, only one tooth 62 defines a cavity 60 in which a soil sensor 108 is installed. In another embodiment, the implement 10 may include a plurality of soil sensors 108. In such an embodiment, several teeth 62 (e.g., either on the same closing disc 50 or on different closing discs 50) may each define a cavity 60 in which a soil sensor 108 is installed.

Figure 5:
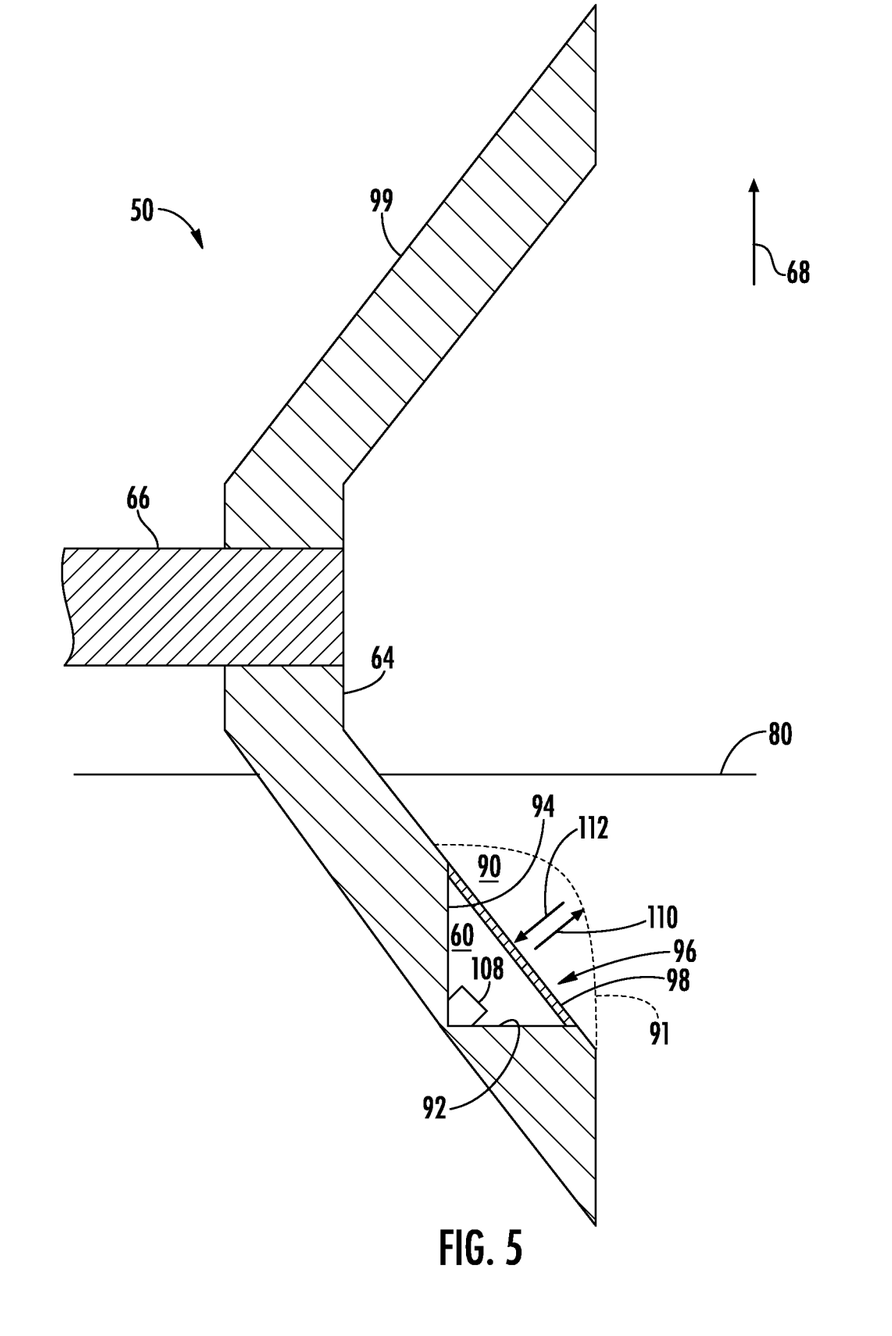
FIG. 5 illustrates a cross-sectional view of another embodiment of a ground-engaging tool of an agriculture in accordance with aspects of the present subject matter, particularly illustrating tool having a concave shape.

Referring now to FIG. 5, a cross-sectional view of another embodiment of the closing disc 50 described above with reference to FIGS. 3 and 4 is illustrated in accordance with aspects of the present subject matter. As shown, the closing disc 50 may be configured the same as or similar to that described above with reference to FIGS. 3 and 4. For instances, the closing disc 50 may define the cavity 60 therein, with the soil sensor 108 being installed or otherwise positioned within the cavity 60. However, as shown in FIG. 5, unlike the above-described embodiment, the closing disc 50 may not include the teeth 62 extending radially outward from the hub 64. Instead, in the embodiment shown in FIG. 5, the closing disc 50 may include a flange 99 extending outward in the radial direction 68 and away from the axle 66 such that the disc 50 has a concave shape or profile. When a force is applied to the closing disc 50 (e.g., via the actuator 102) and the implement 10 is moved across the field, the disc 50 may rotate relative to the soil within the field such that a portion of the flange 99 penetrates the soil surface 80 of the field. The cavity 60 may, in turn, be defined by the portion of the flange 99 that penetrates the soil surface 80 when the implement 10 is moved across the field. However, in alternative embodiments, the closing disc 50 may have any other suitable configuration.

Additionally, it should be appreciated that the configuration of the implement 10 described above and shown in FIGS. 1-5 is provided only to place the present subject matter in an exemplary field of use. Thus, it should be appreciated that the present subject matter may be readily adaptable to any manner of machine configuration.

Figure 6:
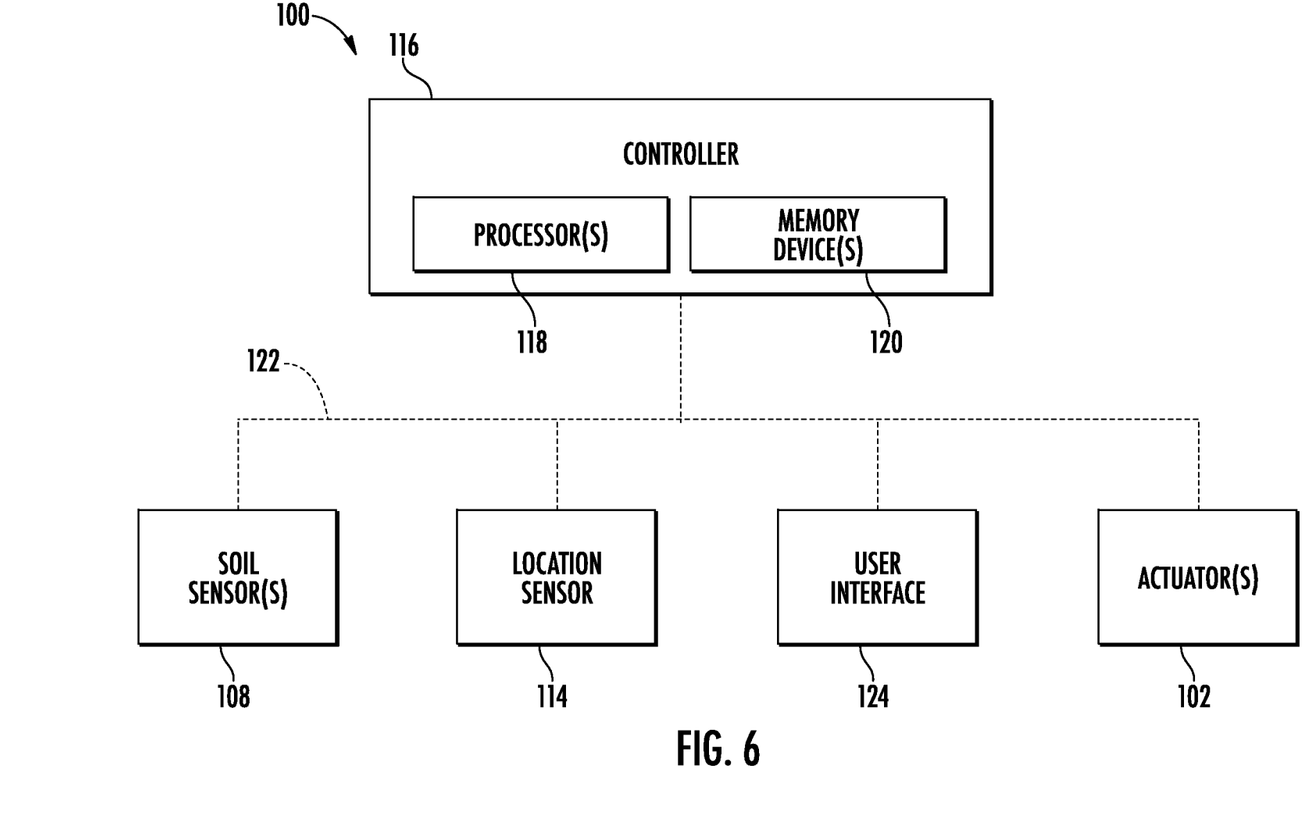
FIG. 6 illustrates a schematic view of one embodiment of a system for monitoring soil composition within a field using an agricultural machine in accordance with aspects of the present subject matter.

Referring now to FIG. 6, a schematic view of one embodiment of a system 100 for monitoring soil composition within a field using an agricultural machine is illustrated in accordance with aspects of the present subject matter. In general, the system 100 will be described herein with reference to the implement 10 described above with reference to FIGS. 1-3. However, it should be appreciated by those of ordinary skill in the art that the disclosed system 100 may generally be utilized with agricultural machines having any other suitable machine configuration.

As shown in FIG. 6, the system 100 may include a location sensor 114 provided in operative association with the implement 10 or an associated agricultural vehicle (not shown). In general, the location sensor 114 may be configured to determine the location of the implement 10 using a satellite navigation positioning system (e.g. a GPS system, a Galileo positioning system, the Global Navigation satellite system (GLONASS), the BeiDou Satellite Navigation and Positioning system, and/or the like). In such an embodiment, the location determined by the location sensor 114 may be transmitted to a controller(s) of the implement 10 and/or the associated vehicle (e.g., in the form coordinates) and stored within the controller's memory for subsequent processing and/or analysis. For instance, based on the known dimensional configuration and/or relative positioning between soil sensor 108 and the location sensor 114, the determined location from the location sensor 114 may be used to geo-locate the soil sensor 108 within the field.

In accordance with aspects of the present subject matter, the system 100 may include a controller 116 positioned on and/or within or otherwise associated with the implement 10 or an associated agricultural vehicle. In general, the controller 116 may comprise any suitable processor-based device known in the art, such as a computing device or any suitable combination of computing devices. Thus, in several embodiments, the controller 116 may include one or more processor(s) 118 and associated memory device(s) 120 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 120 of the controller 116 may generally comprise memory element(s) including, but not limited to, a computer readable medium (e.g., random access memory (RAM)), a computer readable non-volatile medium (e.g., a flash memory), a floppy disc, a compact disc-read only memory (CD-ROM), a magneto-optical disc (MOD), a digital versatile disc (DVD), and/or other suitable memory elements. Such memory device(s) 120 may generally be configured to store suitable computer-readable instructions that, when implemented by the processor(s) 118, configure the controller 116 to perform various computer-implemented functions.

In addition, the controller 116 may also include various other suitable components, such as a communications circuit or module, a network interface, one or more input/output channels, a data/control bus and/or the like, to allow controller 116 to be communicatively coupled to any of the various other system components described herein (e.g., the actuator(s) 102, the soil sensor(s) 108, and/or the location sensor 114). For instance, as shown in FIG. 6, a communicative link or interface 122 (e.g., a data bus) may be provided between the controller 116 and the components 102, 108, 114 to allow the controller 116 to communicate with such components 102, 108, 114 via any suitable communications protocol (e.g., CANBUS).

It should be appreciated that the controller 116 may correspond to an existing controller(s) of the implement 10 and/or an associated agricultural vehicle, itself, or the controller 116 may correspond to a separate processing device. For instance, in one embodiment, the controller 116 may form all or part of a separate plug-in module that may be installed in association with the implement 10 and/or the vehicle to allow for the disclosed systems to be implemented without requiring additional software to be uploaded onto existing control devices of the implement 10 and/or the vehicle. It should also be appreciated that the functions of the controller 116 may be performed by a single processor-based device or may be distributed across any number of processor-based devices, in which instance such devices may be considered to form part of the controller 116. For instance, the functions of the controller 116 may be distributed across multiple application-specific controllers, such as a navigation controller, an implement controller, and/or the like.

Furthermore, in one embodiment, the system 100 may also include a user interface 124. More specifically, the user interface 124 may be configured to provide feedback (e.g., feedback associated with the soil composition) to the operator of the implement 10 and/or the associated agricultural vehicle. As such, the user interface 124 may include one or more feedback devices (not shown), such as display screens, speakers, warning lights, and/or the like, which are configured to provide feedback from the controller 116 to the operator. The user interface 124 may, in turn, be communicatively coupled to the controller 116 via the communicative link 122 to permit the feedback to be transmitted from the controller 116 to the user interface 124. In addition, some embodiments of the user interface 124 may include one or more input devices (not shown), such as touchscreens, keypads, touchpads, knobs, buttons, sliders, switches, mice, microphones, and/or the like, which are configured to receive user inputs from the operator.

In several embodiments, the controller 116 may be configured to determine the composition of the soil within the field across which the implement 10 is being moved. As described above, the implement 10 may include a soil sensor(s) 108 installed or otherwise positioned within a cavity 60 defined by a closing disc(s) 50, such as a tooth/teeth 62 of the disc(s) 50. The soil sensor(s) 108 may be configured to emit the output signal(s) 110 through the corresponding opening(s) 96 and/or the window(s) 98 for reflection off of the soil within the field. Moreover, the soil sensor(s) 108 may be configured to detect the reflected output signal(s) as return signal(s) 112, with one or more parameters of the return signal(s) 112 being indicative of the composition of the soil. In this regard, the controller 116 may be configured to receive data from the soil sensor(s) 108 (e.g., via the communicative link 122) associated with the detected return signal(s) 112. Thereafter, the controller 116 may be configured to analyze/process the received data to determine the composition of the soil within the field. For instance, the controller 116 may include a look-up table(s), suitable mathematical formula, and/or algorithms stored within its memory 120 that correlates the received data to the soil composition of the field. In one embodiment, the controller 116 may be configured to store the determined soil composition of the field within its memory 120 and/or transmit the determined soil composition of the field to a remote device (e.g., a Smartphone, a tablet, a PC, a database server, and/or the like). Such soil composition data may, in turn, be used in planning and/or performing future agricultural operations.

It should be appreciated that the determined soil composition of the field may provide an indication of the amounts and/or concentrations of one or more constituents or components of the soil within the field. For example, in one embodiment, the determined soil composition may provide an indication of the amount and/or concentration of organic matter, residue, and/or moisture within the soil. However, in alternative embodiments, the determined soil composition may provide an indication any other suitable constituent or component of the soil.

Additionally, the controller 116 may be configured to generate a field map illustrating the soil composition at various locations within the field. More specifically, as described above, the controller 116 may be configured to geo-locate the position of the soil sensor(s) 108 within the field and determine the soil composition at the location(s) of the sensor(s) 108 as the implement 10 is being moved across the field. As such, the controller 116 may associate each soil composition determination with the position in the field where the determination was made. Thereafter, the controller 116 may be configured to generate a field map (e.g., a graphical field map) illustrating the soil composition at various positions within the field. For instance, the controller 116 may be configured to execute one or more algorithms stored within its memory 120 that generate the field map based on the data received from the soil sensor(s) 108 and the location sensor 114 (e.g., via the communicative link 122). In one embodiment, the controller 116 may be configured to transmit instructions to the user interface 124 (e.g., the communicative link 122) instructing the user interface 124 to display the field map (e.g., a graphical field map).

Furthermore, the controller 116 may be configured to initiate one or more control actions when the determined soil composition differs from a predetermined range of soil compositions. Such control actions(s) may generally be associated with adjusting the operation of the implement 10 to accommodate changes in the composition of the soil within the field. Specifically, in several embodiments, the controller 116 may be configured to compare the determined soil composition to the predetermined range of soil compositions. The predetermined range may, in turn, be a range of soil compositions (e.g., the amount(s) or concentration(s) of one or more soil components/constituents) of the field for which one or more current operating parameters of the implement 10 are desirable. Thereafter, when the determined soil composition differs from the predetermined range of soil compositions (thereby indicating that the current operating parameter(s) of the implement 10 may not be suited for the current soil composition of the field), the controller 116 may be configured to adjust one or more operating parameters of the implement 10.

In one embodiment, the controller 116 may be configured to automatically adjust the penetration depth of and/or the force being applied to the ground-engaging tools (e.g., the closing discs 50) of the implement 10 when the determined soil composition differs from the predetermined range of soil compositions. In such embodiment, the controller 116 may be configured transmit instructions to the actuator(s) 102 (e.g., via the communicative link 122) instructing the actuator(s) 102 to adjust the penetration depth(s) of and/or the force being applied to the associated closing discs 50. However, in alternative embodiments, the controller 116 may be configured to adjust any other suitable operating parameter(s) of the implement 10, such as the penetration depth(s) of and/or the force(s) being applied to other ground-engaging tools (e.g., the disc opener(s) 44) of the implement 10, the ground speed of the implement 10, and/or the like.

Figure 7:
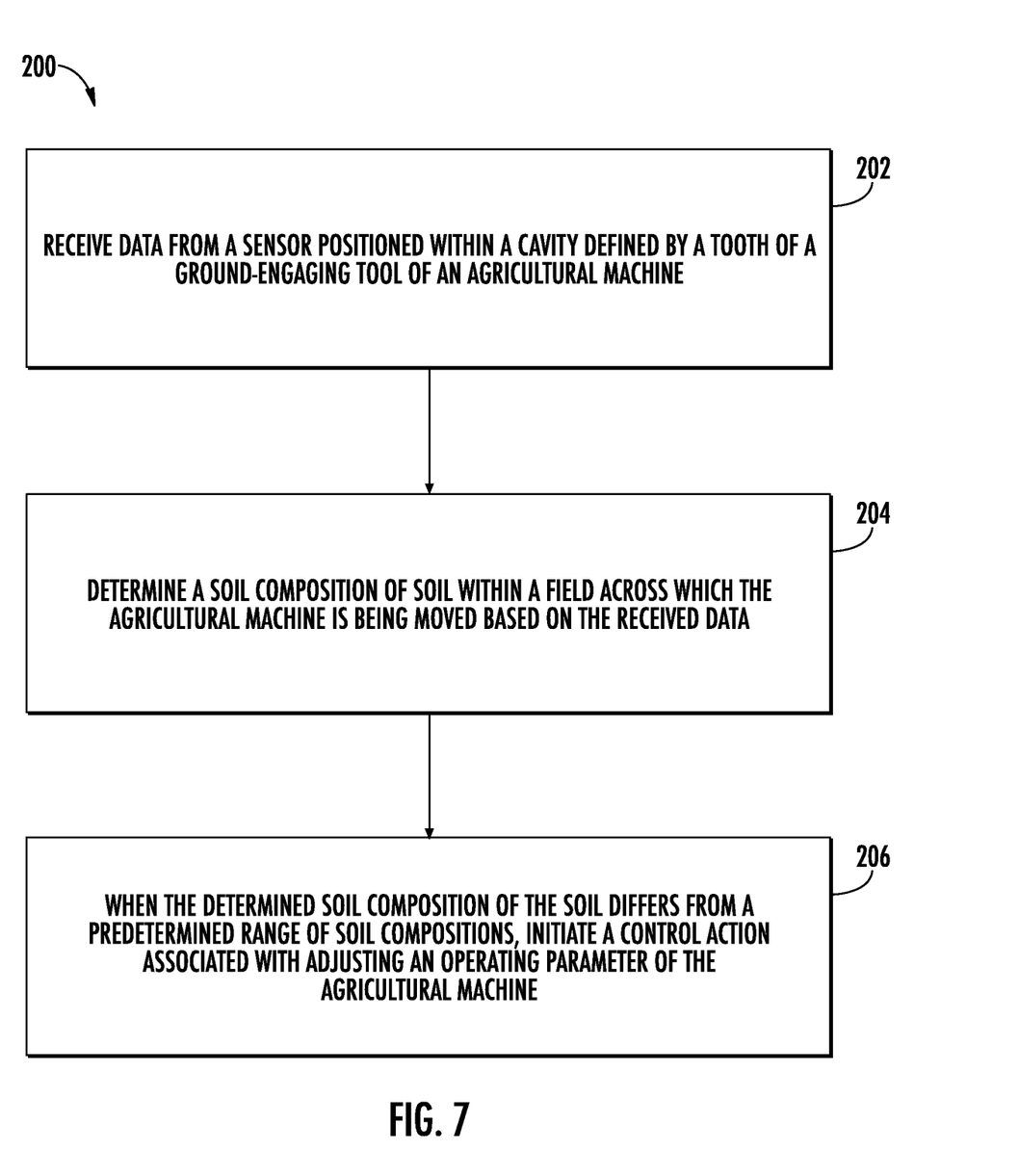
FIG. 7 illustrates a flow diagram of one embodiment of a method for monitoring soil composition within a field using an agricultural machine in accordance with aspects of the present subject matter.

Referring now to FIG. 7, a flow diagram of one embodiment of a method 200 for monitoring soil composition within a field using an agricultural machine is illustrated in accordance with aspects of the present subject matter. In general, the method 200 will be described herein with reference to the agricultural implement 10 and the system 100 described above with reference to FIGS. 1-6. However, it should be appreciated by those of ordinary skill in the art that the disclosed method 200 may generally be implemented with any agricultural machine having any suitable machine configuration and/or any system having any suitable system configuration. In addition, although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 7, at (202), the method 200 may include receiving, with one or more computing devices, data from a sensor positioned within a cavity defined by a tooth of a ground-engaging tool of an agricultural machine. For instance, as described above, the controller 116 may be configured to receive data from a soil sensor 108 positioned within a cavity 60 defined by a tooth 62 of a closing disc 50 of an agricultural implement 10.

Additionally, at (204), the method 200 may include determining, with the one or more computing devices, a soil composition of soil with a field across which the agricultural machine is being moved based on the received data. For instance, as described above, the controller 116 may be configured to determine a soil composition of soil with a field across which the agricultural implement 10 is being moved based on the received data.

Moreover, as shown in FIG. 7, at (206), when the determined soil composition of the soil differs from a predetermined range of soil compositions, the method 200 may include initiating, with the one or more computing devices, a control action associated with adjusting an operating parameter of the agricultural machine. For instance, as described above, when the determined soil composition of the soil differs from a predetermined range of soil compositions, the controller 116 may be configured to initiate one or more control action associated with adjusting one or more operating parameters of the agricultural implement 10. Such operating parameter(s) may include the penetration depth and/or the force being applied to the closing discs 50 of the implement 10.

It is to be understood that the steps of the method 200 are performed by the controller 116 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 116 described herein, such as the method 200, is implemented in software code or instructions which are tangibly stored on a tangible computer readable medium. The controller 116 loads the software code or instructions via a direct interface with the computer readable medium or via a wired and/or wireless network. Upon loading and executing such software code or instructions by the controller 116, the controller 116 may perform any of the functionality of the controller 116 described herein, including any steps of the method 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for monitoring soil composition within a field using an agricultural machine, the system comprising:
   a ground-engaging tool configured to rotate relative to soil within a field as the agricultural machine is moved across the field, the ground-engaging tool including a hub defining a slot extending radially inward from a radially outer edge of the hub, the ground-engaging tool further including a tooth having a mounting end and a tip, the mounting end of the tooth received within the slot, the tooth defining a cavity therein, the cavity including an opening, the ground-engaging tool further including a fastener removably coupling the tooth to the hub; and
   a sensor positioned within the cavity, the sensor configured emit an output signal through the opening for reflection off of the soil within the field, the sensor further configured to detect the reflected output signal as a return signal,
   wherein a parameter of the return signal is indicative of a soil composition of the soil within the field.

2. The system of claim 1, further comprising:
   a window positioned within the opening.

3. The system of claim 1, wherein the output signal comprises an electromagnetic radiation signal.

4. The system of claim 3, wherein the electromagnetic radiation signal comprises at least one of an ultraviolet radiation signal, a near-infrared radiation signal, a mid-infrared radiation signal, or a visible light signal.

5. The system of claim 3, wherein the parameter of the return signal comprises a spectral parameter.

6. The system of claim 2, further comprising:
   a controller communicatively coupled to the sensor, the controller configured to determine the soil composition of the soil based on data received from the sensor associated with the parameter of the return signal.

7. The system of claim 6, wherein the soil composition of the soil comprises at least one of an amount of organic matter within the soil, an amount of crop residue within the soil, or an amount of moisture within the soil.

8. The system of claim 6, wherein the controller is further configured to generate a field map identifying the soil composition of the soil at a plurality of locations within the field.

9. The system of claim 6, wherein the controller is further configured to compare the determined soil composition of the soil to a predetermined range of soil compositions.

10. The system of claim 9, wherein the controller is further configured to initiate an adjustment of a penetration depth of or a force being applied to the ground-engaging tool when the soil determined composition differs from the predetermined range of soil compositions.

11. A method for monitoring soil composition within a field using an agricultural machine, the agricultural machine including a ground-engaging tool configured to rotate relative to soil within a field as the agricultural machine is moved across the field, the ground-engaging tool including a hub defining a slot extending radially inward from a radially outer edge of the hub, the ground-engaging tool further including a tooth having a mounting end and a tip, the mounting end of the tooth received within the slot, the tooth defining a cavity therein, the cavity including an opening, the ground-engaging tool further including a fastener removably coupling the tooth to the hub, the method comprising:

receiving, with one or more computing devices, data from a sensor positioned within the cavity, the sensor configured emit an output signal through the opening for reflection off of the soil within the field, the sensor further configured to detect the reflected output signal as a return signal;

determining, with the one or more computing devices, a soil composition of the soil based on the received data; and when the determined soil composition of the soil differs from a predetermined range of soil compositions, initiating, with the computing device, a control action associated with adjusting an operating parameter of the agricultural machine.

12. The method of claim 11, wherein the soil composition of the soil comprises at least one of an amount of organic matter within the soil, an amount of crop residue within the soil, or an amount of moisture within the soil.

13. The method of claim 11, further comprising:

generating, with the computing device, a field map identifying the soil composition of the soil at a plurality of locations within the field.

14. The method of claim 11, wherein the control action comprises adjusting a penetration depth of or a force being applied to the ground-engaging tool.

* * * * *